(12) United States Patent
Streuer

(10) Patent No.: US 7,674,551 B2
(45) Date of Patent: Mar. 9, 2010

(54) STATE OF CHARGE INDICATOR FOR A BATTERY

(75) Inventor: Peter Streuer, Hannover (DE)

(73) Assignee: VB Autobatterie GmbH, Hannover (DE)

( * ) Notice: Subject to any disclaimer, the term of this patent is extended or adjusted under 35 U.S.C. 154(b) by 86 days.

(21) Appl. No.: 10/452,534

(22) Filed: Jun. 2, 2003

(65) Prior Publication Data

US 2004/0041539 A1  Mar. 4, 2004

(30) Foreign Application Priority Data

Jun. 3, 2002 (DE) .................. 102 24 662

(51) Int. Cl.
    *H01M 10/48* (2006.01)
(52) U.S. Cl. .............. 429/90; 429/91; 429/61; 73/447; 73/291; 320/132
(58) Field of Classification Search ............... 429/13, 429/61, 90, 91; 73/291, 447
    See application file for complete search history.

(56) References Cited

U.S. PATENT DOCUMENTS

| | | | |
|---|---|---|---|
| 3,906,329 A | 9/1975 | Bader | |
| 4,153,867 A | 5/1979 | Jungfer et al. | |
| 4,193,025 A | 3/1980 | Frailing et al. | |
| 4,207,611 A | 6/1980 | Gordon | |
| 4,308,817 A * | 1/1982 | Peterson | 116/215 |
| 4,322,685 A | 3/1982 | Frailing et al. | |
| 4,595,880 A | 6/1986 | Patil | |
| 4,642,600 A | 2/1987 | Gummelt et al. | |
| 4,659,977 A | 4/1987 | Kissel et al. | |
| 4,665,370 A | 5/1987 | Holland | |
| 4,719,427 A | 1/1988 | Morishita et al. | |
| 4,816,736 A | 3/1989 | Dougherty et al. | |
| 4,876,513 A | 10/1989 | Brilmyer et al. | |

(Continued)

FOREIGN PATENT DOCUMENTS

DE   22 42 410   3/1973

(Continued)

OTHER PUBLICATIONS

Intelec '88—Tenth International communications Energy Conference, "A look at the Impedance of a Cell—S.L. DeBardelaben, New York Telephone Company," bearing a designation "Oct. 30-Nov. 2, 1988." (6 sheets).

(Continued)

*Primary Examiner*—Patrick Ryan
*Assistant Examiner*—Ben Lewis
(74) *Attorney, Agent, or Firm*—Lathrop & Clark LLP

(57) ABSTRACT

A state of charge indicator for a battery having a liquid electrolyte includes a viewing rod having an observation surface at a first end, a conical reflection surface at a second end, and a generally cylindrical outer surface intermediate the first end and the second end. The viewing rod includes a central longitudinal axis. The state of charge indicator also includes a ball cage coupled to the second end of the viewing rod through which the electrolyte can flow and at least one ball guide channel provided in the ball cage and arranged obliquely with respect to the central longitudinal axis. The ball guide channel includes an upper boundary surface adjacent the conical reflection surface. The upper boundary surface is smoothly connected to the conical reflection surface.

16 Claims, 2 Drawing Sheets

U.S. PATENT DOCUMENTS

| | | |
|---|---|---|
| 4,888,716 A | 12/1989 | Ueno |
| 4,937,528 A | 6/1990 | Palanisamy |
| 4,943,777 A | 7/1990 | Nakamura et al. |
| 4,952,861 A | 8/1990 | Horn |
| 5,002,840 A | 3/1991 | Klebenow et al. |
| 5,032,825 A | 7/1991 | Kuznicki |
| 5,055,656 A | 10/1991 | Farah et al. |
| 5,079,716 A | 1/1992 | Lenhardt et al. |
| 5,130,699 A | 7/1992 | Reher et al. |
| 5,159,272 A | 10/1992 | Rao et al. |
| 5,162,164 A | 11/1992 | Dougherty et al. |
| 5,204,610 A | 4/1993 | Pierson et al. |
| 5,223,351 A | 6/1993 | Wruck |
| 5,280,231 A | 1/1994 | Kato et al. |
| 5,281,919 A | 1/1994 | Palanisamy |
| 5,316,868 A | 5/1994 | Dougherty et al. |
| 5,321,627 A | 6/1994 | Reher |
| 5,352,968 A | 10/1994 | Reni et al. |
| 5,381,096 A | 1/1995 | Hirzel |
| 5,404,129 A | 4/1995 | Novak et al. |
| 5,412,323 A | 5/1995 | Kato et al. |
| 5,416,402 A | 5/1995 | Reher et al. |
| 5,428,560 A | 6/1995 | Leon et al. |
| 5,439,577 A | 8/1995 | Weres et al. |
| 5,488,283 A | 1/1996 | Dougherty et al. |
| 5,549,984 A | 8/1996 | Dougherty |
| 5,552,642 A | 9/1996 | Dougherty et al. |
| 5,563,496 A | 10/1996 | McClure |
| 5,572,136 A | 11/1996 | Champlin |
| 5,578,915 A | 11/1996 | Crouch, Jr. et al. |
| 5,656,915 A | 8/1997 | Eaves |
| 5,680,050 A | 10/1997 | Kawai et al. |
| 5,698,965 A | 12/1997 | York |
| 5,721,688 A | 2/1998 | Bramwell |
| 5,744,936 A | 4/1998 | Kawakami |
| 5,744,963 A | 4/1998 | Arai et al. |
| 5,761,072 A | 6/1998 | Bardsley, Jr. et al. |
| 5,773,977 A | 6/1998 | Dougherty |
| 5,808,367 A | 9/1998 | Akagi et al. |
| 5,808,445 A | 9/1998 | Aylor et al. |
| 5,818,116 A | 10/1998 | Nakae et al. |
| 5,818,333 A | 10/1998 | Yaffe et al. |
| 5,896,023 A | 4/1999 | Richter |
| 5,898,292 A | 4/1999 | Takemoto et al. |
| 5,936,383 A | 8/1999 | Ng et al. |
| 5,965,954 A | 10/1999 | Johnson et al. |
| 5,977,654 A | 11/1999 | Johnson et al. |
| 5,990,660 A | 11/1999 | Meissner |
| 6,016,047 A | 1/2000 | Notten et al. |
| 6,037,749 A | 3/2000 | Parsonage |
| 6,037,777 A | 3/2000 | Champlin |
| 6,057,666 A | 5/2000 | Dougherty et al. |
| 6,087,808 A | 7/2000 | Pritchard |
| 6,091,325 A | 7/2000 | Zur et al. |
| 6,118,252 A | 9/2000 | Richter |
| 6,118,275 A | 9/2000 | Yoon et al. |
| 6,144,185 A | 11/2000 | Dougherty et al. |
| 6,160,382 A | 12/2000 | Yoon et al. |
| 6,222,341 B1 | 4/2001 | Dougherty et al. |
| 6,268,712 B1 | 7/2001 | Laig-Horstebrock et al. |
| 6,271,642 B1 | 8/2001 | Dougherty et al. |
| 6,296,593 B1 | 10/2001 | Gotou et al. |
| 6,300,763 B1 | 10/2001 | Kwok |
| 6,304,059 B1 | 10/2001 | Chalasani et al. |
| 6,331,762 B1 | 12/2001 | Bertness |
| 6,369,578 B1 | 4/2002 | Crouch, Jr. et al. |
| 6,388,421 B2 | 5/2002 | Abe |
| 6,388,450 B2 | 5/2002 | Richter et al. |
| 6,392,389 B1 | 5/2002 | Kohler |
| 6,392,414 B2 | 5/2002 | Bertness |
| 6,392,415 B2 | 5/2002 | Laig-Horstebrock et al. |
| 6,393,910 B1 * | 5/2002 | Korb et al. ................ 73/447 |
| 6,417,668 B1 | 7/2002 | Howard et al. |
| 6,424,157 B1 | 7/2002 | Gollomp et al. |
| 6,441,585 B1 | 8/2002 | Bertness |
| 6,445,158 B1 | 9/2002 | Bertness et al. |
| 6,452,361 B2 | 9/2002 | Dougherty et al. |
| 6,472,875 B1 | 10/2002 | Meyer |
| 6,495,990 B2 | 12/2002 | Champlin |
| 6,507,194 B2 | 1/2003 | Suzuki |
| 6,515,452 B2 | 2/2003 | Choo |
| 6,515,456 B1 | 2/2003 | Mixon |
| 6,522,148 B2 | 2/2003 | Ochiai et al. |
| 6,534,992 B2 | 3/2003 | Meissner et al. |
| 6,556,019 B2 | 4/2003 | Bertness |
| 6,600,237 B1 | 7/2003 | Meissner |
| 6,600,293 B2 | 7/2003 | Kikuchi |
| 6,608,482 B2 | 8/2003 | Sakai et al. |
| 6,653,818 B2 | 11/2003 | Laig-Horstebrock et al. |
| 2002/0008495 A1 | 1/2002 | Dougherty et al. |
| 2002/0026252 A1 | 2/2002 | Wruck et al. |
| 2002/0031700 A1 | 3/2002 | Wruck et al. |
| 2003/0047366 A1 | 3/2003 | Andrew et al. |
| 2003/0082440 A1 | 5/2003 | Mrotek et al. |
| 2003/0142228 A1 | 7/2003 | Flach et al. |
| 2003/0236656 A1 | 12/2003 | Dougherty |
| 2004/0021468 A1 | 2/2004 | Dougherty et al. |

FOREIGN PATENT DOCUMENTS

| | | |
|---|---|---|
| DE | 2 242 510 C3 | 4/1974 |
| DE | 33 34 128 A1 | 4/1985 |
| DE | 37 12 629 C2 | 10/1987 |
| DE | 38 08 559 A1 | 9/1989 |
| DE | 39 01 680 A1 | 3/1990 |
| DE | 40 07 883 A1 | 9/1991 |
| DE | 38 82 374 T2 | 10/1993 |
| DE | 44 14 134 A1 | 11/1994 |
| DE | 43 39 568 | 5/1995 |
| DE | 689 24 169 T2 | 3/1996 |
| DE | 195 40 827 A1 | 5/1996 |
| DE | 195 43 874 | 5/1996 |
| DE | 197 50 309 A1 | 5/1999 |
| DE | 691 31 276 T2 | 12/1999 |
| DE | 198 47 648 A1 | 4/2000 |
| DE | 694 23 918 T2 | 8/2000 |
| DE | 199 52 693 A1 | 5/2001 |
| DE | 199 60 761 C1 | 5/2001 |
| DE | 93 21 638 U1 | 8/2001 |
| DE | 100 21 161 A1 | 10/2001 |
| DE | 699 00 638 T2 | 8/2002 |
| EP | 0 516 336 B1 | 2/1992 |
| EP | 1 116 958 A2 | 7/2001 |
| WO | WO 97/15839 | 5/1997 |
| WO | WO 99 17128 | 4/1999 |
| WO | WO 99 66340 | 12/1999 |
| WO | WO 00/04620 | 1/2000 |
| WO | WO 01 15023 | 3/2001 |
| WO | WO 03/001224 A1 | 1/2003 |

OTHER PUBLICATIONS

Battery Alert, Ltd., "The Easy-to-Install Battery Deterioration Warning Device", 12 Volt Model (BA101) Advertisement (2 sheets).

Journal of Applied Electrochemistry, vol. 10 No. 1, Jan. 1980—The Impedance of Electrical Storage Cells—N.A. Hampson, s.A.G.R. Karunathilaka, Department of Chemistry, R. Leek, Department of Electronic and Electrical Engineering, University of Technology, Loughborough, Liecestershire, UK (11 sheets).

Battery Evaluation Reports, s.e. Ross Laboratories, Inc., Apr. 1999 (1 page).

HSR-003 Application Notes, Hermetic Switch, Inc., Highway 92, Post Office Box 2220, Chickasha, OK 73023, http://www.hermeticswitch.com/RS_frm.htm, available at least by Jan. 6, 2003 (1 page).

How It Works: Reed Switch Motor, http://members.tripod.com/simplemotor/rsmotor.htm, available at least by Jan. 7, 2003, 4 pages.

Reed Relay Technical & Applications Information, COTO Technology, 55 Dupont Drive, Providence, RI, pgs. http://www.cotorelay.com/ReedTech.pdf, available at least by Jan. 6, 2003, 37-43.

Willibert Schleuter, *Das elektrische Ersatzschaltbild des Bleiakkumulators unter Berücksichtigung erzwungener Elektrolytströmung*, etz Archiv, vol. 4 (1982), Issue 7, pp. 213-218.

Lürkens et al., *Ladezustandsschätzuntt von Bleibatterien mit Hilfe des Kalman-Filters*, etz Archiv, vol. 8 (1986), Issue 7, pp. 231-236.

Brooke, L., "Resin Keeps Batteries Cool", A1 Inside Magazine, Nov. 1998, p. 55.

Hoover, J., "Failure Modes of Batteries Removed from Service", A Presentation at the 107th Convention of Battery Council International, Apr. 30-May 3, 1995, p. 62.

Stan Gibilisco and Neil Sclater, Co-Editors-in-Chief, "Rectifier Bridge," Encyclopedia of Electronics, 2nd Edition, TAB Professional and Reference Books, 1996, pp. 708-711.

Lehman, A., "Electrical Battery Model For Leo Application Based on Absolute Instantaneous State of Charge," Proceedings of the European Space Power Conference held in Madrid, Spain, Oct. 2-6, 1989, ESA Publications, NL, vol. 1, pp. 173-178.

Robbins, Tim & Hawkins, John, "Battery Model For Over-Current Protection Simulation of DC Distribution Systems," Telecommunications Energy Conference, 1994, Intelec '94, 16th International Vancouver, BC, Canada Oct. 30-Nov. 3, 1994, New York, NY, IEEE, pp. 307-314 XP001036407 ISBN: 0-7803-2034-4.

Mayer, D. et al., "Modelling and Analysis of Lead Acid Battery Operation," Ecole des Mines de Paris, XP010092137, pp. 1-3.

Mauracher, P. & Karden, E., "Dynamic Modelling of Lead/Acid Batteries Using Impedance Spectroscopy for Parameter Identification," Journal of Power Sources, Elsevier Sequoia S.A., Lausanne, Ch., vol. 67 (1997) No. 1-2, pp. 69-84, XP004095174 ISSN: 0378-7753, p. 70, line 11; p. 82, line 5, figures 2, 3, 12.

Baert, D & Vervaet, A., "Lead-Acid Battery Model for the Derivation of Peukert's Law," Electrochimica Acta, Elsevier Science Publishers, Barking, GB, vol. 44, No. 20, pp. 3491-3504 XP004168624 ISSN: 0013-4686.

International Search Report for PCT/US02/19760 (international filed Jun. 21, 2002), date of mailing Oct. 10, 2002.

Conference Proceedings, Intelec '86—International Telecommunications Energy Conference, Determining the End of Battery Life—Sheldon DeBardelaben, New York Telephone Company, bearing a designation "Oct. 19-22, 1986." (6 sheets).

Bosch and the New E-Class, Electronic Battery Management System, Focus on Electronics, Nov. 2002 (1 sheet).

Forecast Review, The Battery Man, Nov. 1996 p. 21.

OnGuard™ XT Battery State-of-Health Monitor, 2003 Midtronics, Inc. P/N 156-983A (2 sheets).

* cited by examiner

STATE OF CHARGE INDICATOR FOR A BATTERY

BACKGROUND

The invention relates to a state of charge indicator for a battery which is equipped with a liquid electrolyte, having a transparent viewing rod, which has an observation surface at a first end and has a tip, which is adjacent to a cylindrical outer surface and is formed by a conical reflection surface, at a second end, and having a ball cage which is fitted to the second end of the viewing rod and through which the electrolyte can flow, and in which at least one ball guide channel, which is arranged obliquely to the longitudinal direction of the light rod, is formed for at least one ball with a defined relative density, which extends over the height of the tip of the viewing rod and has end-face and lower boundaries as well as an upper boundary wall which is provided with an interruption for the second end of the viewing rod.

State of charge indicators such as these are based on the fact that the relative density of the electrolyte varies as a function of the state of charge. The relative density of the ball which is guided in the ball guide channel is thus matched to the relative density of the electrolyte, so that the ball is lighter than the electrolyte when the battery is correctly charged, and thus floats in the oblique channel. In contrast, when the battery has been discharged, the relative density of the electrolyte falls below that of the ball, so that the ball sinks downward in the ball guide channel.

According to DE 25 11 426 C2, an oblique ball guide channel is provided, which ends at the tip of the viewing rod. When the ball is floating, because the battery is sufficiently charged, the ball is visible at the end of the viewing rod through the observation surface at the first end. Coloring of the ball thus allows a colored indication (for example green) that the state of charge is correct. Furthermore, the reflection surface at the second end of the viewing rod makes it possible to see whether the battery is filled to a sufficient level with the electrolyte. Specifically, if the electrolyte level has fallen to such an extent that the tip of the viewing rod is no longer immersed in the electrolyte, the conical surfaces at the tip of the viewing rod form a boundary surface with air, so that total reflection occurs on the conical surfaces of the tip of the viewing rod, so that the tip appears as a reflective surface, that is to say, it appears bright. If, on the other hand, the electrolyte level is sufficiently high, the material of the viewing rod is chosen such that the coefficients of refraction of the viewing rod and of the electrolyte are of approximately the same magnitude, so that total reflection no longer occurs. The tip of the viewing rod thus produces an optical connection to the (dark) interior of the battery, so that a dark surface appears on the observation surface (if there is no ball). A ball can, of course, be seen only if the electrolyte level is sufficiently high since, on the one hand, the ball cannot float without any electrolyte and, on the other hand, the reflection surfaces at the tip of the viewing rod result in total reflection, that is to say, observation beyond the light rod is no longer possible. Three different states can thus be identified from the observation surface, namely "bright" for an inadequate electrolyte level, "dark" for an adequate electrolyte level when the battery is discharged, and "color of the ball" for an adequate electrolyte level and an adequate state of charge of the battery.

A state of charge indicator of the type mentioned initially is known from EP 1 120 641 A2. In this document, a ball guide channel is provided, which is intended for guiding two balls with different relative densities. The ball guide channel has a length of about three times the diameter of the balls. The two balls are of different colors, which are not the same as the color of the ball cage. When the battery is discharged, the two balls are located at the lower end of the ball guide channel, so that the upper ball is located under the tip of the viewing rod. If sufficient electrolyte is present, the color of the upper ball (for example red) can thus be seen on the observation surface of the viewing rod. This color indicates that the battery is discharged. With a medium state of charge, the upper (lighter) ball floats up, and disappears from the field of view of the tip of the viewing rod to the upper end of the ball guide channel, while the lower ball does not yet float up, that is to say, it remains at the lower end of the ball guide channel, outside the field of view of the viewing rod. If the electrolyte level is sufficient, the color of the housing (for example yellow) can now be seen on the observation surface. If the state of charge of the battery is good, the lower ball also floats up and strikes against the other ball, which has already floated up, as a result of which it is positioned underneath the tip of the viewing rod. The color of the lower ball (for example green) can be seen on the observation surface, as an indication that the state of charge is good.

If, on the other hand, the electrolyte level has dropped, so that it is no longer in contact with the viewing rod, the total reflection on the conical reflection surfaces of the tip of the viewing rod result in a colorless, bright indication in the observation surface, since the light which is incident through the light rod is totally reflected on the conical reflection surface.

With a state of charge indicator such as this, the balls thus move on a contact line of the upper boundary wall of the ball guide channel, which may be designed with any desired cross section, in particular being circular or square, and has to ensure that the balls are guided in a defined manner at the sides. The upper boundary wall of the ball guide channel is interrupted by a recess, into which the tip of the viewing rod projects. The tip, which is in the form of a point, is in this case located approximately on the imaginary extension line of the upper boundary wall. The angle of the conical reflection surfaces is considerably greater than the inclination angle of the oblique ball guide channel. During operation of a state of charge indicator such as this, it is possible for no unique indications to appear because the balls do not float up completely in the desired manner, but remain jammed in the ball guide channel. It is thus even possible for a partially red and partially green indication to be seen in the observation surface. In general, this can be overcome by knocking the viewing rod. However, it is critical if an incorrect indication that is produced as a result of a ball remaining jammed is not identified and is not overcome by shaking or knocking.

It would thus be desirable to provide an indication for a state of charge indicator of the type mentioned initially that it is less susceptible to malfunctions.

SUMMARY OF THE INVENTION

An exemplary embodiment relates to a state of charge indicator for a battery having a liquid electrolyte. The state of charge indicator includes a viewing rod having an observation surface at a first end; a conical reflection surface at a second end, and a generally cylindrical outer surface intermediate the first end and the second end. The viewing rod includes a central longitudinal axis. The state of charge indicator also includes a ball cage coupled to the second end of the viewing rod through which the electrolyte can flow and at least one ball guide channel provided in the ball cage and arranged obliquely with respect to the central longitudinal axis. The ball guide channel includes an upper boundary surface adjacent the conical reflection surface. The upper boundary surface is smoothly connected to the conical reflection surface.

Another exemplary embodiment relates to a state of charge indicator for a battery having a liquid electrolyte. The state of charge indicator includes a viewing rod having a conical reflection surface and a ball cage through which the electrolyte can flow coupled to the viewing rod. A channel is provided in the ball cage that includes an upper boundary surface adjacent the conical reflection surface. The upper boundary surface is generally co-linear with the conical reflection surface.

BRIEF DESCRIPTION OF THE DRAWINGS

The invention will be explained in more detail in the following text with reference to an exemplary embodiment which is illustrated in the drawing, in which:

FIG. 1b shows a stepped horizontal section along the line A-A in FIG. 1a.

DETAILED DESCRIPTION OF THE PREFERRED AND EXEMPLARY EMBODIMENTS

According to an exemplary embodiment, a state of charge indicator of the type mentioned initially is provided that includes an upper boundary wall that is connected smoothly to a conical reflection surface at the junction to the cylindrical outer surface.

The invention is based on the knowledge that the reason the balls remain jammed should not be looked for in the lift forces, which are small due to the minor differences in the relative density, and which do not, for example, overcome adhesion forces, but primarily in the space which is formed above the pointed tip of the viewing rod with the upper boundary wall of the ball guide channel, with this space being formed in particular by the different inclination angles of the ball guide channel on the one hand and of the conical reflection surface of the viewing rod on the other hand. This results in a stepped edge for the linear guidance of the balls as they float up, on which the ball can remain jammed as it floats up. According to the exemplary embodiment, the upper boundary wall is now smoothly connected to the conical reflection surface. This is done by making the angle of the conical reflection surface preferably precisely the same as the inclination angle of the ball guide channel, so that the upper boundary wall is aligned with the conical reflection surface. Minor angular discrepancies of a few angular degrees (<10°) are, of course, not critical.

The upper boundary wall should be connected to the conical reflection surface with as small an intermediate space as possible, which according to an exemplary embodiment is less than ¼ of the ball diameter, and according to a preferred embodiment is less than 1/10 of the ball diameter. In practice, a connection can be produced which has virtually no intermediate space.

The design according to the invention is preferably produced in that the diameter of the cylindrical outer surface of the viewing rod is designed such that it is reduced in size in steps at the second end, so that the viewing rod can be inserted on the step, which is formed in the outer surface, on a corresponding annular shoulder of the ball cage, thus allowing the smooth junction of the conical reflection surface to the upper boundary wall. In contrast, in the known embodiments, provision was made for the annular shoulder of the ball cage to be matched to the gradient of the conical reflection surface, in order in this way to allow the viewing rod to be inserted in a defined manner into the ball cage. This resulted in the necessity to make the angle of the conical reflection surface considerably greater than the inclination angle of the ball guide channel.

It has also been found that it is expedient to design the tip of the viewing rod and those edges of the upper boundary wall which are adjacent to the viewing rod to be rounded, since the balls preferably remain jammed on sharp edges and tips.

Figure 1A:
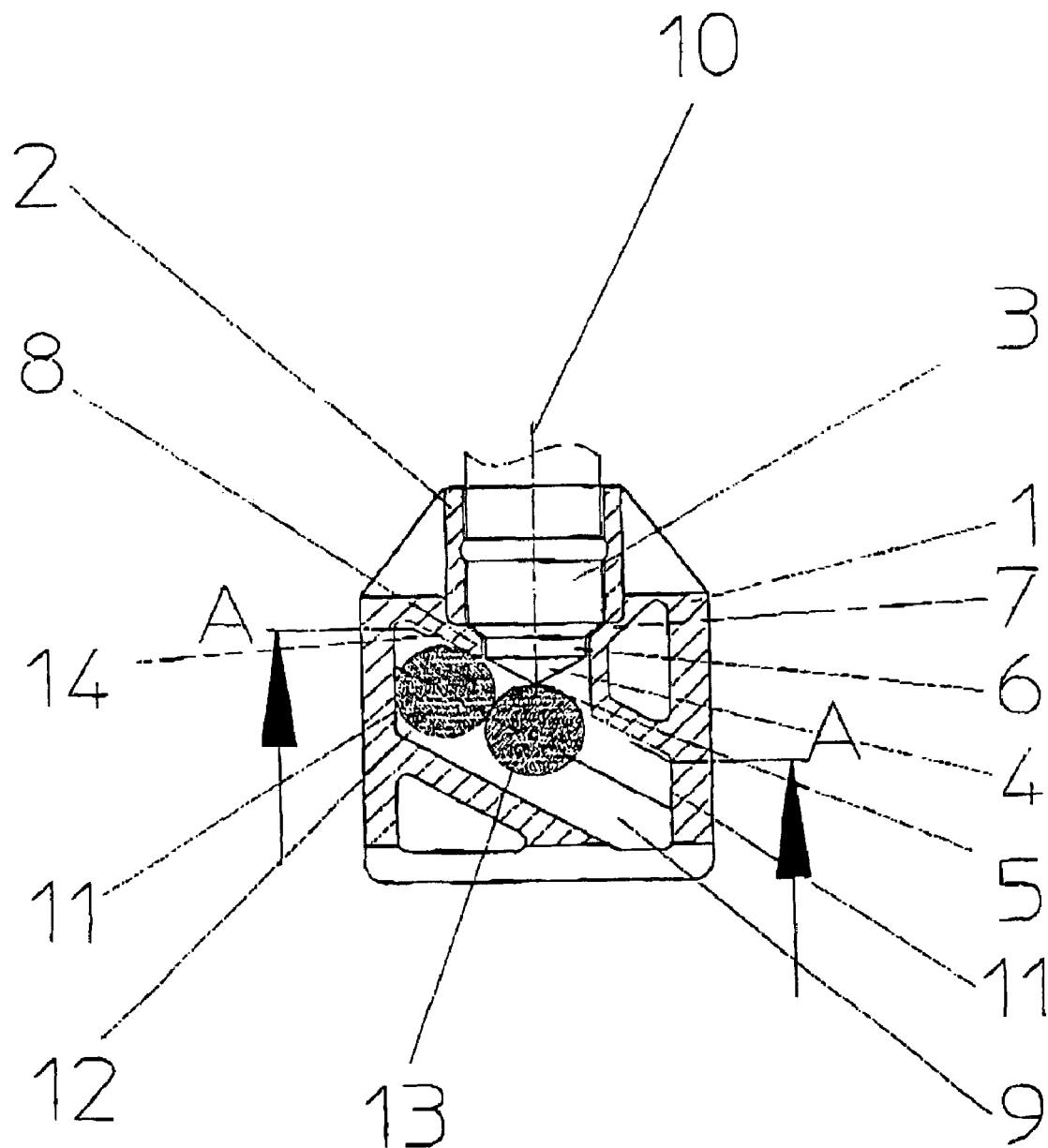
FIG. 1a shows a vertical section through a ball cage with a tip of a viewing rod inserted.

FIG. 1a shows a ball cage 1 through which an electrolyte can flow and which has a cylindrical holder 2 for a viewing rod 3. The viewing rod is provided at its lower end with a conical reflection surface 4, which ends in a pointed tip 5. The viewing rod 3 has a circular cylindrical outer surface 6, which is provided with a reduced diameter, via a step 7, toward the conical reflection surface 4. A correspondingly covered guide 8 is provided in the ball cage 1.

The ball cage 1 has a ball guide channel 9 which forms an angle of about 45° with a longitudinal axis 10 (e.g., a central longitudinal axis) of the viewing rod 3, and whose length is bounded by end walls 11. A first ball 12 and a second ball 13 are located in the ball guide channel 9. The balls are preferably of the same size and are of different colors. The first ball 12 is preferably red, while the second ball 13 is preferably green.

The housing of the ball cage 1 is preferably likewise colored, in particular yellow. The first ball 12 has a lower relative density than the second ball 13. As the density of the electrolyte increases, the first ball 12 thus floats up first of all, while the second ball 13 still remains in its lower rest position. As the density of the electrolyte rises further during charging, the second ball 13 also floats up.

According to a preferred embodiment, the length of the ball guide channel 9 is three times the diameter of the balls 12, 13, which are of equal size.

The upper boundary wall 14 has a recess 15 (see FIG. 1b), into which the end of the viewing rod 3 projects. The end of the viewing rod 3 is inserted into the recess 15 such that the conical reflection surface 6 merges smoothly into the upper boundary wall 14 of the ball guide channel 9 in the upward direction from the tip 5. As can be seen from FIG. 1b, which offers a view of the upper boundary wall 14 from underneath, the upper boundary wall 14 is adjacent to the conical reflection surface 4 on a guide line 16, virtually without any intermediate space.

In addition to the smooth transition without any intermediate space, the angle of the conical reflection surface 4 is preferably identical to the inclination angle of the upper boundary wall 14 of the ball guide channel 9, so that the conical reflection surface 4 and the upper boundary wall 14 are completely aligned with one another on the guide line 16 as far as the tip 5 (e.g., the upper boundary wall and the conical reflection surface are generally co-linear).

Figure 1B:
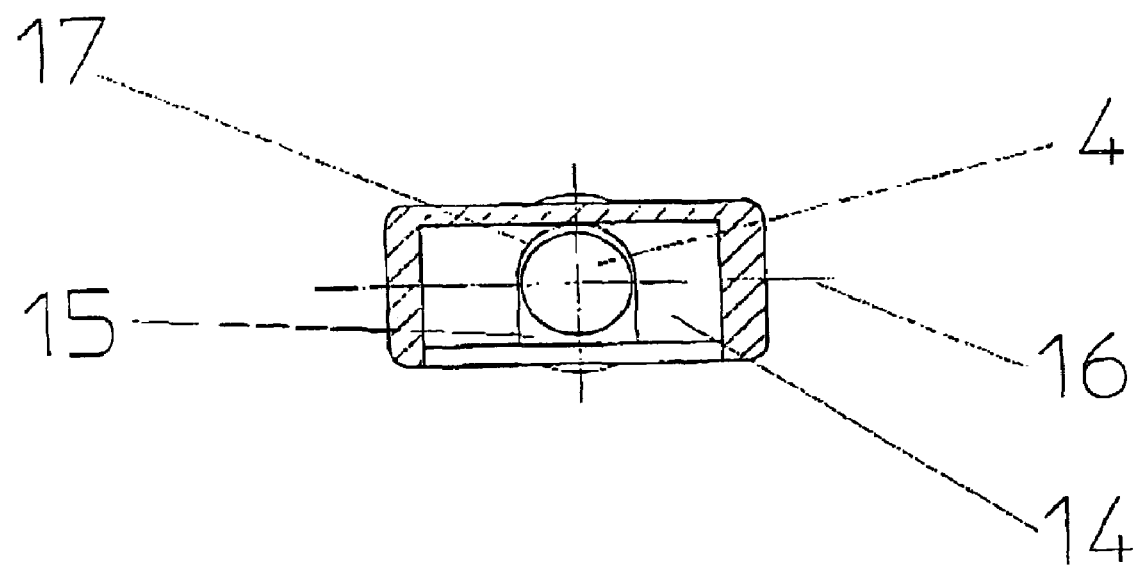

FIG. 1b shows an edge 17 of the recess 15. This edge 17 and the tip 5 may preferably be somewhat rounded, in order to avoid sharp edges on the guide line 16 for the balls 12, 13.

Priority application DE 102 24 662.9 filed on Jun. 3, 2002, including the specification, drawing, claims, and abstract, is incorporated herein by reference in its entirety.

It is important to note that the construction and arrangement of the elements of the energy store as shown and described in the preferred and other exemplary embodiments is illustrative only. Although only a few embodiments of the present inventions have been described in detail in this disclosure, those skilled in the art who review this disclosure will readily appreciate that many modifications are possible without materially departing from the novel teachings and advantages of the subject matter recited herein. It should be noted that the elements and/or assemblies of the system may be constructed from any of a wide variety of materials that provide sufficient strength or durability. Other substitutions, modifications, changes and omissions may be made in the design, operating conditions and arrangement of the preferred and other exemplary embodiments without departing from the scope of the present invention.

What is claimed is:

1. A state of charge indicator for a battery having a liquid electrolyte comprising:
    a viewing rod having an observation surface at a first end, a conical reflection surface at a second end, and a generally cylindrical outer surface intermediate the first end and the second end, the viewing rod including a central longitudinal axis;
    a ball cage coupled to the second end of the viewing rod through which the electrolyte can flow;
    at least one ball guide channel provided in the ball cage and arranged obliquely with respect to the central longitudinal axis such that an upper portion of the ball guide channel extends upward from the conical reflection surface and a lower portion of the ball guide channel extends downward from the conical reflection surface, the upper portion of the ball guide channel
    including an upper boundary surface adjacent the conical reflection surface; and at least one ball provided in the ball guide channel; wherein the upper boundary surface of the upper portion of the ball guide channel extends upward from and above the conical reflection surface such that it is smoothly connected to the conical reflection surface and is generally co-linear with the conical reflection surface on a guide line; and
    wherein the at least one ball is configured to move upward toward the upper portion when the density of the electrolyte increases: and
    wherein a distance between the upper boundary surface and the conical reflection surface is less than ¼ of the diameter of the ball provided in the ball guide channel.

2. The state of charge indicator of claim 1 wherein a distance between the upper boundary surface and the conical reflection surface is less than ¹⁄₁₀ of the diameter of the ball.

3. The state of charge indicator of claim 1 wherein the cylindrical outer surface has a diameter configured such that it is reduced in size in steps at the second end.

4. The state of charge indicator of claim 1 wherein the viewing rod surface has a tip at the second end adjacent the conical reflection surface that has a rounded shape.

5. The state of charge indicator of claim 1 wherein upper boundary wall surface includes an edge adjacent to the viewing rod that includes a rounded shape.

6. The state of charge indicator of claim 1 wherein two balls with different relative densities are located in the ball guide channel.

7. The state of charge indicator of claim 6 wherein a section of the ball guide channel extends beyond the viewing rod and has a length which corresponds to the diameter of the ball the has the lower relative density.

8. The state of charge indicator of claim 6 wherein the two balls have the same dimensions.

9. The state of charge indicator of claim 6 wherein the length of the ball guide channel is three times the diameter of the balls.

10. The state of charge indicator of claim 1 wherein the diameter of the cylindrical outer surface corresponds to the diameter of the ball provided in the ball guide channel.

11. A state of charge indicator for a battery having a liquid electrolyte comprising:
    a viewing rod having a conical reflection surface;
    a ball cage through which the electrolyte can flow coupled to the viewing rod;
    a channel provided in the ball cage, the channel including an upper boundary surface adjacent the conical reflection surface and an upper portion that extends above the conical reflection surface; and
    at least one ball provided in the channel;
    wherein the upper boundary surface extends upward from and above the conical reflection surface and is generally co-linear with the conical reflection surface; and
    wherein the ball cage is configured to allow the at least one ball to move into the upper portion of the channel: and
    wherein a distance between the upper boundary surface and the conical reflection surface is less than ¼ of the diameter of the ball provided in the ball guide channel.

12. The state of charge indicator of claim 11 wherein the upper boundary surface and the conical reflection surface are separated by a distance that is less than ¹⁄₁₀ of a diameter of a ball provided in the channel.

13. The state of charge indicator of claim 11 wherein the viewing rod has a central longitudinal axis and the channel is provided at an oblique angle with respect to the central longitudinal axis.

14. The state of charge indicator of claim 11 wherein the viewing rod includes a rounded tip adjacent the conical reflection surface.

15. The state of charge indicator of claim 11 wherein two balls are provided in the channel, the two balls having different relative densities.

16. The state of charge indicator of claim 15 wherein the balls have different colors.

* * * * *